(12) United States Patent
Smart et al.

(10) Patent No.: US 7,300,750 B2
(45) Date of Patent: Nov. 27, 2007

(54) ANALYTE ASSAY DEVICE WITH PREABSORBING ZONE

(75) Inventors: David Smart, Moira (GB); Patrick Considine, Co. Galway (IE); Marie Eagleton, Co. Louth (IE)

(73) Assignee: Oran DX Limited, Oranmore (IE)

( * ) Notice: Subject to any disclaimer, the term of this patent is extended or adjusted under 35 U.S.C. 154(b) by 126 days.

(21) Appl. No.: 10/149,628

(22) PCT Filed: Dec. 11, 2000

(86) PCT No.: PCT/BG00/04714

§ 371 (c)(1),
(2), (4) Date: Sep. 23, 2002

(87) PCT Pub. No.: WO01/42788

PCT Pub. Date: Jun. 14, 2001

(65) Prior Publication Data

US 2003/0049658 A1    Mar. 13, 2003

(30) Foreign Application Priority Data

Dec. 10, 1999  (GB)  ................................. 9929272.4

(51) Int. Cl.
*G01N 33/53* (2006.01)

(52) U.S. Cl. .................... 435/5; 436/514; 436/518; 436/169; 436/170; 436/177; 436/178; 436/808; 436/810; 436/7.1; 436/2; 436/4; 436/7.92; 436/805; 436/287.1; 436/962; 436/970; 422/56; 422/61; 422/101

(58) Field of Classification Search ................ 436/514, 436/518, 169, 170, 177, 178, 808, 810; 435/2, 435/4, 7.1, 7.92, 805, 287.1, 287.2, 287.7, 435/287.8, 287.9, 962, 970; 422/56–61, 422/101

See application file for complete search history.

(56) References Cited

U.S. PATENT DOCUMENTS

| | | | | |
|---|---|---|---|---|
| 4,459,359 A | * | 7/1984 | Neurath | ........................ 435/5 |
| 5,879,895 A | * | 3/1999 | Babiuk et al. | ............... 435/7.1 |
| 5,939,331 A | * | 8/1999 | Burd et al. | ................. 436/518 |
| 5,945,345 A | * | 8/1999 | Blatt et al. | ................... 436/518 |
| 6,008,059 A | * | 12/1999 | Schrier et al. | .............. 436/518 |

FOREIGN PATENT DOCUMENTS

| | | |
|---|---|---|
| EP | 0088636 A | 9/1983 |
| EP | 0262328 A | 4/1988 |
| GB | 2300914 A | 11/1996 |
| WO | WO 9517676 A | 6/1995 |
| WO | WO 9535502 A | 12/1995 |

* cited by examiner

*Primary Examiner*—Bao-Thuy L. Nguyen
(74) *Attorney, Agent, or Firm*—Drinker, Biddle & Reath LLP.

(57) ABSTRACT

The present invention provides an assay device for detection of an analyte which is a member of a specific binding partner in a sample, the assay device comprising a sample application zone, a preabsorbing zone and a specific binding zone. The device can provide a HSV-2 specific assay by preabsorbing HSV-1 antibodies in the preabsorbing zone.

16 Claims, 1 Drawing Sheet

ANALYTE ASSAY DEVICE WITH PREABSORBING ZONE

Figure 1:
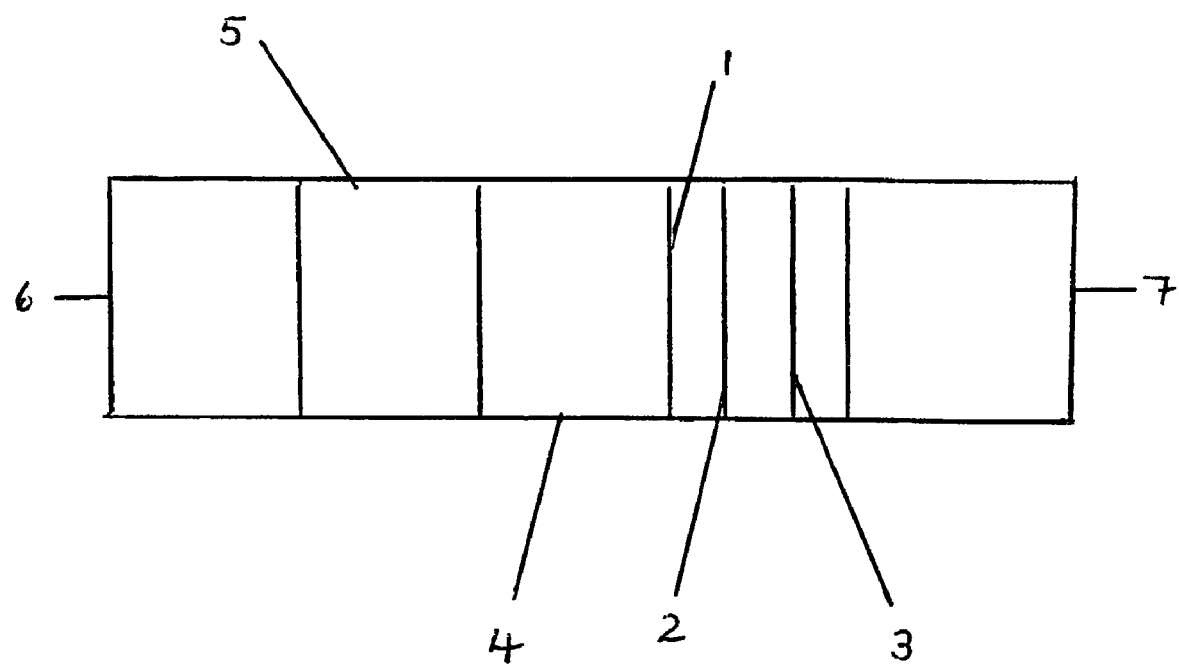

The present invention relates to an improved ligand-receptor assay and a method of enhancing the specificity of assays which involve detection of an analyte which constitutes one member of a pair of specific binding partners (SBP) by detection of its binding to the other member of said pair.

Assay based tests involving SBP are in widespread use by healthcare providers and the public for diagnosis of a variety of conditions.

The present invention seeks to enhance the specificity of assays for the presence of ligands which are one member of a pair of SBP by effecting the removal of potentially cross-reactive ligands prior to analysis of the first ligand.

In the field many assays utilise one member of a pair of SBP bound to a solid phase with which a sample suspected of containing the second member of the pair of SBP is then interacted. Any second member of the SBP which is bound to the first member of the SBP which in turn is bound to the solid-phase antigen is then detected to constitute a positive result in the test.

Many assays seek to determine the presence or absence of one member of a pair of SBP by detecting the binding of this first member to its binding partner. The disadvantage of this method is that the sample utilised in the assay may also contain other ligands which are potentially capable of binding to the second member of the pair of SBP. For example, an assay may involve the detection of antibodies to a particular antigenic species possibly in the presence of other antibodies which are potentially cross reactive with the antigenic species. Unless the binding of the member of the pair of SBP to which the member of the pair of SBP suspected of being present in the sample binds during the assay is highly specific to the member of the pair of SBP suspected of being present in the sample the presence of potentially cross-reactive ligands can compromise the specificity of such assays, leading to the occurrence of false positive results and, potentially, incorrect or inappropriate clinical management of a patient arising from use of such a false result. Several methods have been employed to enhance the specificity of the members of pairs of SBP used in these tests. These include use of synthetic peptide/non-peptide mimics of the member of the pair of SBP or, in the case where the member of the pair of SBP is a protein, use of recombinant protein analogues of the member of the pair of SBP. The potential disadvantage of such SBP analogues is that they may not be identical to the SBP encountered by the patient. There is, therefore, a potential for assays using such artificial SBP to elicit falsely negative results and, potentially, incorrect or inappropriate clinical management of a patient arising from use of such a false result.

It is an object of the present invention to provide an improved binding assay.

The present invention describes an assay format wherein a sample suspected of containing one member of a pair of SBP, the "analyte", is first exposed to one or more moieties which are capable of binding members of other SBP which could potentially cross-react with the other member of the pair of SBP to which the analyte binds, before then being exposed to said second member of the pair of SBP of which the analyte is the first member. Analyte bound to its specific binding partner is then detected using a suitably-labelled second binding partner which binds to the analyte at a site other than the binding site for the analyte and the first SPB.

Preferably, such an assay shall be composed of a membrane capable of conducting fluid flow, this membrane comprising of a sample application zone, a fluid absorbent zone, a line or lines of immobilised analyte antigens and one or more lines of immobilised receptor moieties which function as preabsorbing groups.

Preferably the line or lines of said immobilised preabsorbing groups and analyte antigens are interposed between the sample application zone and the fluid absorption zone.

Fluid flow along the membrane from said sample application zone to towards the fluid absorption zone is preferably facilitated by means of capillary action.

Preferably such movement of the sample will result in the analyte antibodies and cross-reacting antibodies to first contact the preabsorbing groups and subsequently the analyte antigens.

Also preferably, the line or lines of immobilised analyte antigens are interposed between the line or lines of immobilised preabsorbing groups and the fluid absorption zone.

The application of such lines of immobilised moieties should be such that lateral fluid flow along the membrane causes all the components present in the fluid to contact the lines of immobilised moieties.

Samples assayed by means of the present invention may be selected from, but not limited to whole blood, serum, plasma, interstitial fluid, semen, seminal plasma, urine and saliva.

Detection of analyte antibodies, which are bound to the membrane by complexation with their respective analyte antigens is by means of a suitably labelled reagent, which is capable of binding to said SBP complex, wherein this labelled reagent can be detected.

The device can similarity detect analyte antigens by complexation with immobilised antibodies.

Such labelling reagent may be selected from the group consisting of, but not limited to, those which dispose a visually detectable moiety at the site of binding, those which dispose a fluorescent moiety, whereby such a moiety can be visualised either by fluorescence spectrometry or visually upon application of light at an appropriate wavelength to cause fluorescence of the flurophore employed.

Detection said labelled reagent may be by means a catalytic moiety which is attached to the labelled reagent, wherein the catalytic moiety is subsequently exposed to a substrate wherein a visually discernible, fluorescent, or chemiluminescent product is generated by the action of said catalytic moiety.

Colloidal gold and any combination of coloured latex can be used for labelling.

A general embodiment of the invention may comprise
1. Forming an assay for the detection of antibodies ("analyte antibodies") which may be present in a sample; such antibodies being the specific binding partners of one or more particular antigens ("analyte antigens"), such an assay being composed of a membrane capable of conducting fluid flow and incorporating a sample application zone, a fluid absorbent zone, a line or lines of immobilised analyte antigens and one or more lines of immobilised receptor moieties ("preabsorbing groups") capable of binding antibodies ("cross-reacting antibodies") which may be present in the sample and which are potentially capable of binding to sites on the analyte antigens other than the site or sites on the analyte antigens which bind the analyte antibodies and such that the line or lines of immobilised preabsorbing groups and analyte antigens are interposed between the sample application zone and the fluid absorption zone, and the line or lines of immobilised analyte antigens are interposed between the line or lines of immobilised preabsorbing groups and the fluid absorption zone. Lines of immobilised moieties are applied to the membrane such that lateral fluid flow along the membrane causes all components present in the fluid to contact the lines of immobilised moieties.

2. Applying a sample which may be one of a group which includes but is not limited to whole blood, serum, plasma, interstitial fluid, semen, seminal plasma, urine, or saliva to the sample application zone on the membrane such that fluid flow along the membrane by capillary action from the sample application zone towards the fluid absorption zone causes analyte antibodies and cross-reacting antibodies to first contact the preabsorbing groups and subsequently the analyte antigens.

3. Contacting the membrane with a suitably labelled reagent capable of binding to any analyte antibodies bound to the membrane by complexation with their respective analyte antigens and indicating the presence of such bound antibodies such indicia including but not being limited to Deposition of a visually discernible moiety at the site of antibody binding Deposition of a fluorescent moiety at the site of antibody binding such moiety being visualised either by fluorescence spectrometry or visually upon application of light at the wavelength necessary to cause fluorescence of the fluorophore employed Production of a visually discernible, fluorescent or chemiluminescent product at the site of antibody binding by the action of a catalytic moiety attached to the labelled reagent which is used to detect bound antibodies and which is subsequently exposed to a suitable substrate wherein said visually discernible, fluorescent or chemiluminescent product is generated by the action of the catalytic moiety on the substrate.

A preferred embodiment of the invention may comprise

1. Forming an assay for the detection of antibodies specific to Herpes simplex virus type 2 (HSV-2) which may be present in a patient sample such assay being composed of a membrane capable of conducting fluid flow and incorporating a sample application zone, a fluid absorbent zone, a line of antigen derived from Herpes simplex virus type 1 (HSV-1) and a line of antigen derived from HSV-2 such that the lines of HSV-1 and HSV-2 derived antigens are interposed between the sample application zone and the fluid absorption zone and the line of antigen derived from HSV-2 is interposed between the line of antigen derived from HSV-1 and the fluid absorption zone. Lines of immobilised antigens are applied to the membrane such that lateral fluid flow along the membrane causes all components present in the fluid to contact the lines of immobilised antigens.

2. Applying a whole blood sample to the sample application zone on the membrane such that fluid flow along the membrane by capillary action from the sample application zone towards the fluid absorption zone causes antibodies specific for HSV-2 and potentially cross-reacting antibodies to first contact the HSV-1 derived antigen and subsequently the HSV-2 derived antigen.

3. Contacting the membrane with a detector reagent comprising an anti-human immunoglobulin antibody conjugated to colloidal gold such that binding of the detector reagent to sample derived membrane bound antibodies leads to the deposition of a visibly discernible complex at the site on the membrane where the antibodies are bound.

4. Determining the presence or absence of antibodies to HSV-2 in the patient sample by visual discernment of the presence or absence of color at the site of immobilisation on the membrane of the HSV-2 antigen.

ADVANTAGES OF THE INVENTION OVER PRESENT TECHNOLOGY

This invention enables the development of assays which utilise the native members of pairs of SBPs whilst, minimising false results due to the presence of other ligands which might be capable of binding to the member of the pair of SBP utilised in the assay. An additional advantage in the general embodiment described is that no sample pre-treatment is required to effect this improvement.

Advantages of the Invention in the Specific Embodiment

The detection of type specific antibodies to Herpes simplex virus type 2 (HSV-2) in a patient sample is complicated by the close antigenic similarity between HSV-2 and HSV-1, the latter very commonly occurring in most populations (60-100% prevalence in adult populations). The detection of type specific antibodies involves utilisation of type specific antigens, however, there are no antigens either in HSV-1 or HSV-2 which are totally unique to the individual type. Even antigens which are generally considered to be type specific (for example glycoprotein G) show a degree of similarity. For this reason, several attempts have been made to construct type specific serological tests for HSV-2 which utilise regions of certain HSV-2 antigens which are truly unique to the individual type. Such antigen fragments may be constructed using recombinant gene technology or as synthetic peptides. The problem with such antigens is that they may not accurately or completely represent the full range of epitopes presented to a patient by the antigen in its native state (i.e. during the course of an infection). Therefore, such antigens may not bind certain patient antibodies produced in response to an infection and as such, lead to assays of reduced sensitivity.

The advantage of the invention in this specific embodiment is that it enable the manufacture of serological tests for antibodies to HSV-2 which utilise a truly native antigen (i.e. the protein purified from the HSV-2 organism) whilst removing those potentially cross-reactive antibodies derived from an HSV-1 infection which could compromise the specificity of such an assay.

Use of the present invention will make the results of assays more reliable by significantly reducing the occurrence of false results due to the presence of other ligands which might be capable of binding to the member of the pair of SBP utilised in the assay. Thus diagnoses based on the results of such tests would also be more reliable.

In practice, the following points should also be accounted for.

In the specific embodiment of the invention described above, a design specification shall be written which shall ideally but not exclusively describe the use of potentially cross-reacting antigens to improve the specificity of a serological assay for antibodies to herpes simplex type 2 (HSV-2). This shall involve 1. A permeable membrane strip which incorporates a sample application zone, lines of HSV-1 and HSV-2 antigen and anti-human immunoglobulin G antibody and a zone of an absorbent capable of absorbing all the liquid applied to membrane.

2. The strip is housed in a casing of suitable material with apertures to enable the application of a sample to the sample application zone, the visualisation of the membrane in the region of the HSV-2 antigen and anti-human antibody and the application of a detector reagent such that the sample application aperture is between the detector reagent aperture and the visualisation aperture.
3. The antigen lines, antibody line and absorbent zone are laterally spaced such that a sample applied in the sample application zone first contacts the HSV-1 antigen, then the HSV-2 antigen, then the anti-human antibody, then the absorbent zone as it diffuses along the membrane.
4. A detector reagent comprising a colloidal gold labelled anti-human immunoglobulin antibody capable of binding to antibodies which bind to the immobilised HSV-2 antigen and to the antihuman antibody is then added to the membrane at the detector reagent aperture.
5. The labelled detector reagent will then diffuse along the membrane and bind to immobilised antibodies bound to the HSV-2 antigen and antihuman antibody thereby enabling visualisation of the bound antibodies in the visualisation aperture of the device.

Development of the technology and application of this invention will center around the following areas; Further prototype devices based upon this design will be constructed and the diagnostic performance verified, manufacturing product specifications shall be developed. Product will be manufactured according to the manufacturing specifications. The product will be evaluated in clinical trials in appropriate target populations. The product shall be placed into the market.

A general embodiment of the invention given above describes the use of the invention in a test to detect antibodies to specific antigens. Since the detector reagent will also detect antibodies which bind to the preabsorbing antigen or antigens, the invention also relates to an embodiment wherein the preabsorbing antigen may be placed such that it is visible in the visualisation window of the device and the test separately measure antibodies to these other antigens. In addition, the order of spacing of the various binding moieties on the membrane indicates whether a binding moiety is being used as a preabsorbing group. For example, in a specific embodiment of the invention given above which describes the use of the invention in a test to detect specific antibodies to HSV-2, it would be possible to construct a test utilising a line of HSV-1 antigen to preabsorb cross-reacting antibodies and thereby improve the specificity of the HSV-2 test. However, if the HSV-1 line were placed between the sample application zone and the HSV-2 line then its function would include preabsorbing potentially cross-reactive antibodies to improve the performance of the HSV-2 test.

In specifying the nature of the preabsorbing moiety (eg. natural source molecule, recombinant protein), it is possible to utilise a number of technologies for developing alternative preabsorbing group mimics (eg. anti-idiotypic antibodies, non-peptide mimetics). The nature of the preabsorbing groups need not be specified.

An example of the invention is illustrated in the following example and with reference to the accompanying FIGURE.

FIG. 1 illustrates diagramatically a nonlimiting device according to the invention.

EXAMPLE

Preabsorbing antigen, Herpes Simplex Virus type 1 (HSV-1) recombinent glycoprotein G, 0.2 ul/cm (Biokit, Spain), were printed on to nitrocellulose (Whatman Immunopore 5.0 u) membrane strips (0.5×20 mm) supported on polyethylene strips in a fashion well known to those skilled in the art. Test antigen, partially purified native Herpes simplex Virus Type 2 (HSV-2), 40 ng/cm protein (Biokit, Spain), were printed downstream of this line in relation to liquid flow along the membrane. The membrane was dried, blocked with a solution containing sucrose (4%), BSA (0.3%) and Tween (0.01%) and dried.

A pad (conjugate pad), 0.5×10 mm, (Millipore Quick Release) was impregnated with a solution containing polyvinylalcohol, BSA and Triton. After drying, the pad was sprayed with a solution containing goat anti human IgG (Sigma) conjugated to gold sol (prepared by a method known by those skilled in the art). After drying, the processed pad was attached to the membrane (see FIG. 1).

A liquid absorbing pad (absorbent pad) 0.5×20 mm (S&S) was placed on the membrane (see FIG. 1)

A second liquid absorbing pad 0.5×20 mm (S&S) was placed in contact with the conjugate pad (see FIG. 1).

A 20 ul sample of human serum was added to the membrane between the conjugate pad and the preabsorbing antigen. The sample moved laterally sequentially across the Preabsorbing antigen line, Test antigen line, and the Control line. After 30 seconds, buffer, 150 ul PBS, was added to the buffer pad. The liquid moved onto the conjugate pad and releases the goat anti human IgG-gold conjugate on to the membrane. The conjugate moved laterally sequentially across the membrane, passing through the Preabsorbing antigen line, Test antigen line, and the Control line and then onto the absorption pad.

If the sample contained IgG antibodies to HSV-2, these were complexed with the Test gG2 antigen.

Potentially cross contaminating, HSV-1 lgG antibodies to gG1, were completed with the Preabsorbing antigen. Residual lgG antibodies in the sample were complexed with the Control line. If IgG antibodies are complexed at the Preabsorbing antigen line, Test antigen line, and the Control line then these will react with the anti-human IgG-gold conjugate yielding a pink/red line.

Serum samples containing IgG antibodies to HSV-1 and HSV-2 glycoprotein G were assayed with the test device. Coloured lines were observed at the Preabsorbing antigen, Test antigen, and Control respectfully.

Serum samples containing only HSV-1 IgG antibodies yielded only two coloured lines Preabsorbing antigen, and the Control lines respectfully i.e. a negative test for HSV-2 antibody result.

If devices were manufactured omitting the preabsorbing antigens and these devices were used to assay serum samples containing only HSV-1 IgG antibodies, some devices yielded two coloured lines, Preabsorbtion, Test and Control, i.e. a false positive result.

In FIG. 1 the labels represent:
1. Preabsorbing Antigen
2. Test Antigen
3. Control
4. Membrane
5. Conjugate Pad
6. Buffer Pad
7. Absorption Pad.

The invention claimed is:
1. An assay device capable of detecting an analyte which is a member of a pair of specific binding partners, the device comprising a pre-absorbing zone and a specific binding zone;
wherein the specific binding zone comprises a specific binding partner immobilized thereon which specifically binds the analyte; wherein the pre-absorbing zone comprises at least one immobilised antigen or immobilised antibody, at least one receptor moiety, or combination thereof, which function as pre-absorbing group(s) immobilised in said pre-absorbing zone, the pre-absorbing groups designed such that they bind an interferent in the sample rather than the analyte, said interferent being immunologically cross-reactive with the specific binding partner in the specific binding zone; wherein a sample suspected of containing the analyte passes through the pre-absorbing zone prior to entering the specific binding zone.

2. The device as claimed in claim 1 which is a membrane based device which conducts fluid flow.

3. The device as claimed in claim 1 comprising a sample application zone, at least one line of immobilised pre-absorbing groups and a specific binding zone wherein the at least one line of pre-absorbing groups is interposed between the sample application zone and the specific binding zone.

4. The device as claimed in claim 3 further comprising a fluid absorption zone, wherein the at least one line of pre-absorbing groups is interposed between the sample application zone and the fluid absorption zone.

5. The device as claimed in claim 1 wherein the sample movement is facilitated by capillary action.

6. The device as claimed in claim 1 wherein the sample is selected from the group consisting of whole blood, serum, plasma, interstitial fluid, semen, seminal plasma, urine and saliva.

7. A method of detecting an analyte which is a member of a pair of specific binding partners in a sample using the assay device as claimed in claim 1, said method comprising the steps
  (a) exposing a sample suspected of containing the analyte to at least one pre-absorbing moiety in the pre-absorbing zone which binds an interferent which is immunologically cross-reactive with the specific binding partner of the analyte ; then
  (b) exposing the sample which has passed through the pre-absorbing zone to the specific binding partner of the analyte in the specific binding zone; and
  (c) detecting binding of said analyte to said specific binding partner.

8. The assay device according to claim 1, wherein the analyte and the interferent are antibodies and the specific binding partner in the specific binding zone and the pre-absorbing group(s) are antigens.

9. The assay device according to claim 1, wherein the analyte and the interferent are antigens and the specific binding partner in the specific binding zone and the pre-absorbing group(s) are antibodies.

10. The assay device according to claim 1, wherein the specific binding partner in the specific binding zone specifically binds antibodies specific to Herpes simplex virus Type 2 and the pre-absorbing groups specifically bind antibodies specific to Herpes simplex virus Type 1.

11. The assay device according to claim 1, wherein the device further comprises a detector reagent, wherein said detector reagent can bind to an interferent bound to said pre-absorbing group and can bind to an analyte bound to said specific binding partner immobilized on the specific binding zone.

12. The assay device according to claim 11, wherein the binding of said detector reagent to said pre-absorbing group and to said specific binding partner is visualisable.

13. The device according to claim 12, wherein the device comprises a conjugate pad, on which the detector reagent is stored, wherein said conjugate pad is positioned such that fluid may flow from said conjugate pad to said pre-absorbing zone and said specific binding zone.

14. The method according to claim 7 wherein, in step (c), said binding of said analyte to said specific binding partner is detected by detecting binding of a detector reagent to said analyte, wherein said detector reagent is capable of binding to interferent bound to said pre-absorbing moiety.

15. The method according to claim 14 including the step of detecting the presence or absence of binding of the detector reagent to interferent bound to said pre-absorbing moiety.

16. The method according to claim 14, wherein the step of detecting binding of the analyte to the specific binding partner comprises exposing:
  (i) the specific binding zone, and
  (ii) the pre-absorbing zone to the detector reagent and visualizing (A) binding of the detector reagent to analyte bound to the specific binding partner and (B) the presence or absence of binding of the detector reagent to said interferent bound to said pre-absorbing moiety.

* * * * *